United States Patent [19]

Burdick et al.

[11] Patent Number: 4,801,504

[45] Date of Patent: Jan. 31, 1989

[54] FLUORESCENT LABELS HAVING A POLYSACCHARIDE BOUND TO POLYMERIC PARTICLES

[75] Inventors: Brent A. Burdick; Susan J. Danielson, both of Rochester, N.Y.

[73] Assignee: Eastman Kodak Company, Rochester, N.Y.

[21] Appl. No.: 100,513

[22] Filed: Sep. 24, 1987

Related U.S. Application Data

[62] Division of Ser. No. 713,206, Mar. 18, 1985, Pat. No. 4,719,182.

[51] Int. Cl.$^4$ ................................................ B32B 5/16
[52] U.S. Cl. ...................................... 428/403; 436/529; 436/530; 436/533; 436/534; 436/546
[58] Field of Search ................. 428/403, 690; 436/529, 436/533, 530, 534, 546

[56] References Cited

U.S. PATENT DOCUMENTS

| | | | |
|---|---|---|---|
| 4,259,313 | 3/1981 | Frank | 436/546 |
| 4,264,766 | 4/1981 | Fischer | 424/12 |
| 4,283,382 | 8/1981 | Frank | 436/546 |
| 4,452,773 | 6/1984 | Molday | 424/1.1 |
| 4,604,364 | 8/1986 | Kosak | 436/800 |

OTHER PUBLICATIONS

Bankert, J. Immuno., 123(6), pp. 2466–2474, (1979).

Primary Examiner—Robert J. Warden
Assistant Examiner—Robert Benson
Attorney, Agent, or Firm—J. Lanny Tucker

[57] ABSTRACT

Fluorescent labels comprise a polysaccharide bound to a polymeric particle which contains a fluorescent rare earth chelate. These labels can be attached to any of a variety of physiologically reactive species to provide labeled species which have improved stability in aqueous solutions. The labeled species are particularly useful in specific binding assays to determine an immunologically reactive ligand, e.g. a hapten, in either solution or dry analytical techniques.

4 Claims, No Drawings

FLUORESCENT LABELS HAVING A POLYSACCHARIDE BOUND TO POLYMERIC PARTICLES

This is a division of application Ser. No. 713,206 filed Nov. 18, 1985 now U.S. Pat. No. 4,719,182.

FIELD OF THE INVENTION

This invention relates to fluorescent labels and to fluorescent labeled physiologically reactive species useful in biomedical studies and clinical chemistry determinations. These labels and labeled species are particularly useful in specific binding assays, e.g. immunoassays, to determine a specific binding ligand, such as a hapten, in human biological fluids.

BACKGROUND OF THE INVENTION

In the fields of medicine and clinical chemistry, many studies and determinations of physiologically reactive species, e.g. cells, protein, enzymes, cofactors, nucleic acids, substrates, antigens, antibodies, etc. are carried out using "labels" which facilitate the detection or separation of the materials under observation at low concentration. In one such application, the diagnosis of pathological conditions and the detection of drugs or narcotics in humans and animals is often carried out using labeled materials in specific binding assays using competitive binding principles.

Whenever labels are used, sensitivity is of prime importance due to the generally low levels of biological species that are measured. Procedures carried out using radiometric labels generally do not have sufficient sensitivity for many low level analytes. In addition, radiometric labels suffer from the drawbacks of short useful life and handling hazards.

Labeling with magnetic iron oxide has also been proposed, as described in U.S. Pat. No. 4,452,773 (issued June 5, 1984 to Molday). The sensitivity of such labels is also limited, and their use in labeling biological species requires expensive equipment and tedious procedures.

Fluorescent spectroscopy, one of the most sensitive and versatile of the optical analytical techniques, has become increasingly popular in recent years to overcome drawbacks of other labeling techniques. In fluorescence spectroscopy, a sample containing a fluorescent species is irradiated with light of known spectral distribution within the exitation spectrum of the target fluorescent species. The intensity of the resulting characteristic emission spectrum of the fluorescent target molecules is determined and is related to the number of target molecules in the sample. Fluorescent spectroscopy is used extensively for studies of protein structure, bacterial cell wall reactions and conformational changes in enzymes, as well as for determinations of an immunologically reactive ligand in a specific binding assay.

Fluorescent labels comprising chelates of a rare earth element incorporated into polymeric particles of a loadable latex are described in U.S. Pat. Nos. 4,259,313 (issued Mar. 31, 1981 to Frank et al) and related 4,283,382 (issued Aug. 11, 1981 to Frank et al). These labels exhibit improved efficiency in fluorescence and are particularly useful for immunoassays. The polymeric particles serve as carriers for immunologically reactive species directly attached thereto.

Our colleagues, J. R. Schaeffer, T. J. Chen and M. A. Schen, have discovered that certain polymers provide exceptionally stable fluorescent labels. These labels are the subject of copending and commonly assigned U.S. Ser. No. 713,202 filed Mar. 18, 1985 and entitled STABILIZED FLUORESCENT RARE EARTH LABELS AND LABELED PHYSIOLOGICALLY REACTIVE SPECIES. However, these polymers comprise a small class of materials composed of recurring units derived from certain combination of monomers.

Although the labels of the Frank et al references represent a breakthrough in clinical chemistry because of their improved fluorescence efficiency, there is a need to render the broad class of polymeric labels described therein more stable in aqueous solutions. The labels of Frank et al generally tend to agglutinate spontaneously and to settle out of solution. They therefore have a shortened storage life. They also demonstrate a tendency to agglutinate prematurely during an assay. The improvements discovered by Schaeffer et al are limited to a small class of polymeric labels. Hence, it is desirable to have fluorescent labels which avoid the above problems.

SUMMARY OF THE INVENTION

We have discovered novel labels and labeled species having improved stability in aqueous solutions (e.g. biological fluids). These materials do not prematurely agglomerte, can be stored for long periods of time and require minimal resuspension prior to use. These materials are particularly useful in specific binding assays, but they can also be used in a variety of biomedical studies where labeling of any physiologically reactive species is desired. These labels exhibit the desirably high sensitivity which accompanies the use of fluorescence spectroscopy.

The unexpected and significantly improved properties of the materials of this invention are achieved by the use of a polysaccharide arm to link a labeled polymeric particle with a physiologically reactive species. This polysaccharide arm also enhances the sensitivity of the assay to analytes which might otherwise be undetectable because they are dwarfed by the much larger polymeric particle.

Therefore, in accordance with this invention, a fluorescent label comprises a polysaccharide bound to a polymeric particle which is derived from a loadable latex having a discontinuous phase which consists essentially of a polymer prepared from one or more ethylenically unsaturated polymerizable monomers, and an aqueous phase. The polymeric particle has incorporated therein a fluorescent rare earth chelate.

This invention also provides a fluorescent labeled physiologically reactive species. This labeled species comprises a conjugate of a physiologically reactive species bound to a polysaccharide, which conjugate is bound to the polymeric particle described above through the polysaccharide. In preferred embodiments, this labeled species is a labeled immunologically reactive ligand analog.

Further, this invention provides a dry analytical element which comprises an absorbent carrier material and the fluorescent labeled physiologically reactive species described above. In preferred embodiments, the absorbent material is a porous spreading zone carried on a support.

This invention also provides a method of labeling a physiologically reactive species comprising attaching the species to the fluorescent label described above.

Still further, this invention comprises a method for the determination of an immunologically reactive ligand in an aqueous liquid. The method comprises the steps of:

A. in the presence of a receptor for the ligand, contacting a sample of the liquid with a fluorescent labeled immunologically reactive ligand analog as described above, to form a complex between the receptor and the ligand analog, and B. fluorometrically detecting the ligand analog.

DETAILED DESCRIPTION OF THE INVENTION

The fluorescent labels of this invention can be used as probes (also known as labels) for a variety of biomedical studies and clinical chemistry determinations. They can be used to label cells or other physiologically reactive species including proteins, nucleic acids (e.g. DNA), enzymes and their substrates, cofactors, viruses, leukocytes, growth factors, antigens, haptens or drugs, antibodies, metabolites, hormones, plant lectins, toxins, radio-isotopes and other pharmacalogical agents and their receptors, and other binding substances enabling the detection of such substances. Examples of these substances are extensive and well known in the art.

The labels are particularly useful in specific binding assays to determine an analyte (i.e. immunologically reactive species). In these assays, the species to be determined is attached to the label and the labeled species is placed in competition with unlabeled species for reaction with a common reactant. The species to be determined is referred to herein as the ligand, and the labeled species as the ligand analog. Compounds which specifically recognize the ligand and ligand analog and react to form complexes with them are referred to herein as receptors.

In performing one such assay, the ligand is placed in competition with the ligand analog for binding to the receptor. Unknown concentrations of the ligand are inferred from the measured signal of the labeled ligand analog. The reaction proceeds as follows: ligand+labeled ligand analog+receptor⇌ligand−receptor+labeled ligand analog−receptor.

In preferred embodiments of this invention, the ligand is an antigen or antibody, the labeled ligand analog is a labeled antigen or antibody and the specific binding assay is an immunoassay. In the following discussion and presentation of examples, reference will be made primarily to these preferred embodiments, but it is to be understood that the scope of the invention is inclusive of any other specific binding assay.

The labels of this invention comprise a polysaccharide bound to a latex polymeric particle which contain a rare earth chelate. The polysaccharide is bound to the particle by any suitable means, e.g. covalent bonding or absorption, but preferably, covalent bonding is used.

Polysaccharides useful in the practice of this invention are carbohydrates containing at least 3 simple sugar molecules and include, but are not limited to, crosslinked polysaccharides, a polysaccharide derivative which can be hydrolyzed by an endohydrolase, lipopolysaccharides (polysaccharides containing fatty acids), cellulose and cellulosic derivatives, carboxymethylated polysacharides, inulin and the like. The polysaccharides can be obtained from natural or synthetic sources. Particularly useful polysaccharides are generically known as dextrans and lipopolysacchariees each having a and molecular weight of at least about 1000, preferably from about $10^4$ to about $10^7$. Lipopolysaccharides are described in, for example, an article by Tsumita et al, *J. Exp. Med.*, 119, pp. 1017–1025 (1964). Dextrans are polysaccharides containing a backbone of D-glucose units linked predominantly α-D (1-6). Representative dextrans are described in the articles by Jeanes et al, *J.A.C.S.*, 76, pp. 5041–5052 (1954) and Bankert et al, *J. Immun.*, 123(6), pp. 2466–2474 (1979). Many dextrans are commercially available. Dextrans are most preferred in the practice of this invention. The polysaccharides have functional groups (e.g. hydroxy groups) which are reactive, or can be rendered reactive, with proteins or other biological molecules.

The polysaccharide is bound to the surface of latex polymer particles which contain a rare earth chelate. These polymer particles are prepared with loadable latices which are described in detail in U.S. Pat. Nos. 4,259,313 and 4,283,382 (noted above). Preferably, these labels are "aqueous-stabilized" meaning that the fluorescence of the chelate is not quenched in an aqueous environment.

In general, any fluorescent rare earth chelate which demonstrates fluorescent behavior is useful in the practice of this invention. In particular, the chelate comprises a rare earth metal (i.e. a lanthanide metal) such as europium or terbium. Europium is most preferred.

The chelate also includes a suitable chelating agent. Particularly useful chelating agents include 1,3-diketones (e.g. acetylacetonate, p-benzoylacetonate, p-benzoylbenzoate, trifluoro-2-furylacetylacetone, etc.), phthalates, naphthoates (e.g. dinaphthoylmethide, etc.), dipyridines (e.g. 2,2'-bypyridine-1,1'-dioxide, 4,4'-dimethyl-2,2'-dipyridine, etc.), terpyridines (e.g. 2,2',6',2''-terpyridine, etc.) and phenanthrolines (e.g. o-phenanthroline isothiocyanate, etc.). Other chelating agents are known to those skilled in the art. The 1,3-diketones are preferred.

The details of "loading" the latices useful in this invention are given in the Frank et al patents noted above. Generally, the chelate is incorporated in the polymer particles by gradually increasing the hydrophilicity of a solution of a hydrophobe in a water-miscible solvent in the presence of uncoagulated, undissolved loadable polymeric latex particles to a point at which substantially no hydrophobe remains dissolved in the watermiscible solvent. Up to about 7.5% (based on polymer weight) of chelate can be "loaded" or imbibed into the polymer particles in this manner. The concentration of chelate in the polymer particles can be varied to some extent depending upon the particular use of the label intended. The preparation of a fluorescent label of this invention is described in Example 1 below.

Loadable polymer latices useful herein are those which include a polymeric discontinuous phase (particles) which consists essentially of one or more polymers prepared from one or more ethylenically unsaturated polymerizable monomers, and an aqueous continuous phase. The polymer particles of these latices generally have an average diameter of from about 0.01 to about 2 μm, and preferably from about 0.1 to about 0.5 μm.

Particularly useful latices are those comprising polymers comprising (a) from 0 to 100 weight percent of units derived from one or more vinyl aromatic monomers (i.e. substituted or unsubstituted styrenes and vinyl naphthyls), (b) from 0 to about 90 weight percent of units derived from one or more ethylenically unsaturated monomers of the structure:

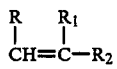

wherein R is hydrogen or substituted or unsubstituted alkyl, preferably of 1 to 5 carbon atoms (e.g. methyl, ethyl, chloromethyl, hydroxymethyl, isopropyl, etc.), $R_1$ is hydrogen or methyl, and $R_2$ is hydrogen, halogen (e.g. chloro, bromo, etc.), substituted or unsubstituted alkyl, preferably of 1 to 4 carbon atoms (e.g. methyl, hydroxymethyl, ethyl, isopropyl, butyl, etc.), cyano,

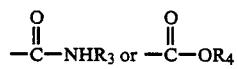

wherein $R_3$ is hydrogen or $R_4$, and $R_4$ is a substituted or unsubstituted aliphatic group preferably containing from 1 to 10 carbon atoms, and optionally one or more oxygen ether or nitrogen amido atoms in the chain (e.g. alkyl, alkylene-oxy-alkyl, alkylene-carbonyloxyalkyl, alkylene-carbonamido, hydroxyalkyl, etc.), optionally substituted with one or more amino (primary, secondary, tertiary or quaternary) groups, and (c) from 0 to 10 weight percent of units derived from one or more ethylenically unsaturated monomers containing one or more sulfonic acid or carboxy groups, or an ammonium or alkali metal (e.g. sodium, potassium, etc.) salt thereof.

Representative monomers of group (a) include styrene, α-methylstyrene, p-bromostyrene, styrene sulfonic acid, sodium salt, vinyltoluene, 2-vinylmesitylene, chloroethylsulfonyl methyl styrene, 1-vinylnaphthylene, and others known in the art. Representative monomers of group (b) include acrylamide, methacrylamide, n-butyl acrylate, methyl methacrylate, acrylonitrile, propyl acrylate, 2-hydroxyethyl acrylate, 2-hydroxypropyl methacrylate, N-isopropylacrylamide, vinyl chloride, vinylbromide, and others known in the art. Representative monomers of group (c) include acrylic acid, methacrylic acid, 2-acrylamido-2-methylpropane sulfonic acid, sodium salt, 3-methacryloyloxypropane-1-sulfonic acid, sodium salt, 2-methacrylamido-2,2-dimethylpropane sulfonic acid, sodium salt, 2-(methacryloyloxy)ethyltrimethylammonium methosulfate, vinyl sulfonic acid, potassium salt, and others known to one skilled in the art.

Preferred polymers are composed of from about 40 to 100 weight percent of units derived from a styrene monomer (substituted or unsubstituted as described hereinabove), and from 0 to about 60 weight percent of units derived from monomers (b) above wherein R is hydrogen, $R_1$ is hydrogen or methyl, and $R_2$ is cyano,

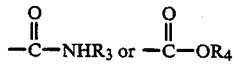

wherein $R_3$ is hydrogen or $R_4$ and $R_4$ is substituted or unsubstituted alkyl, preferably of 1 to 10 carbon atoms (e.g. methyl, hydroxymethyl, ethyl, isopropyl, t-butyl, hexyl, etc.).

In addition to the units of preferred monomers described above, the polymers can comprise units derived from one or more ethylenically unsaturated monomers other than those of (a), (b), or (c) described above. Such monomers are known to one skilled in polymer chemistry.

Particularly useful polymers which can contain a label and be attached to a polysaccharide are taken from the specific class of polymers described in copending and commonly assigned U.S. patent application Ser. No. 713,202 of Schaeffer et al, noted above.

The loadable polymer latices useful in preparing the fluorescent labels can be prepared using well known emulsion polymerization techniques. Generally, they are prepared using free radical initiated reactions of the monomers dispersed in an aqueous medium with one or more appropriate surfactants.

The fluorescent label can be prepared by mixing the polysaccharide and a polymer latex containing the rare earth chelate for a suitable time to facilitate absorption of the polysaccharide on the surface of the polymer particles. To covalently bond the polysaccharide to the polymer particles, either one or both components may be chemically modified to facilitate reaction of polysaccharide reaction sites with corresponding reaction sites on the polymer particle surfaces.

The fluorescent labeled physiologically reactive species of this invention can be prepared in either of two ways. One way is to react the species with the fluorescent label described above to covalently bond the species to the polysaccharide. This procedure may require chemical modification of either the fluorescent label (i.e. the polysaccharide linking arm of the label) or the species, or both.

Alternatively, the physiologically reactive species and polysaccharide can be reacted to form a polysaccharide-species conjugate before the polysaccharide is attached to the polymeric particles containing the chelate. Either or both reactants may be modified in order to promote the reaction. For example, some or all hydroxyl groups of the polysaccharide may be oxidized to provide pendant aldehyde groups. The species, for example, may contain or be modified to contain amine groups which can react with the aldehyde groups of the polysaccharide to form a Schiff base bonding the polysaccharide to the species. Details of preparing a representative conjugate with polysaccharides and thyroxine are described below in Examples 1 and 3.

Once having prepared a polysaccharide-species conjugate, it can be attached to the surface of the polymeric particles through the polysaccharide linking arm to form a labeled physiologically reactive species by any suitable technique known to one skilled in the art. For example, the conjugate can be absorbed to the polymer particles, or covalently bonded thereto. Generally, the conjugate and latex are mixed together for a suitable time (e.g. up to 72 hours) to facilitate absorption of conjugate on the surface of the polymer particles. Details of the preparation of a representative labeled species are provided in Examples 1 and 3 below.

The fluorescent labeled specific binding ligand analog of this invention can be used in specific binding immunoassays, particularly those which utilize temporal resolution of the specific detecting signal to distinguish it from background. In this immunoassay, a sample of test aqueous liquid is excited in an intermittent fashion and information is accepted only during the dark cycle when the long-lived fluorescent label is still emitting strongly but when other sources of fluorescence have decayed. Discontinuous excitation can be achieved in a variety of ways, including pulsed laser, mechanical chopping or a continuous excitation beam, moving the sample in and out of the excitation beam, etc. In general, fluorescent immunoassay techniques are known in the art.

In the practice of this invention, the labeled ligand analog indicates the amount of unknown ligand in the test sample. Either the bound or unbound fraction of labeled ligand analog can be measured.

To accomplish a specific binding assay, physical separation of bound and unbound ligand can be carried out using conventional techniques.

In a solution assay, the fluorescent labeled specific binding ligand analog is generally present in a concentration of up to about 1, and preferably from about 0.01 to about 1, mg/dl of solution. The receptor corresponding to the ligand (or analyte) to be determined is generally present in an amount of up to about 1, and preferably from about $10^{-6}$ to about 1 g/dl of solution. Other materials, e.g. buffers, surfactants, etc. can be included in conventional amounts if desired.

The ligand analog and method of this invention are adaptable to both solution and dry element assays. The ligand analog, along with its receptor, can be provided as part of a diagnostic test kit for either dry or solution assays. For solution assays, the kit components can be supplied as lyophilized reagents in individual packets having predetermined amounts. Alternatively, they can be provided in bottled or otherwise packaged solutions sufficient in size for one or more assays. Other optional reagents can also be supplied in the kit along with suitable assay utensils or containers for performing the assay. A dry analytical element (described below) containing a ligand analog can also be supplied as part of the diagnostic kit.

Generally, the ligand analog, its corresponding receptor and test sample believed to contain a ligand analyte are physically contacted and mixed in a suitable container (e.g. test tube, petrie dish, beaker, cuvette, etc.). The resulting solution can be incubated, if desired, for a time (e.g. 0.5–4 hours) at a temperature of up to about 37° C. to promote the formation of a complex of the receptor with both the ligand analog and the ligand in the test sample. The sample is then evaluated by measuring the fluorescence of bound (i.e. complexed) or unbound (i.e. noncomplexed) label. Such an evaluation can be done visually or with suitable fluorometric detection equipment and procedures.

The method of this invention can also be utilized with a dry analytical element which can be composed of an absorbent carrier material, i.e. thin sheet of self-supporting absorbent or bibulous material, such as a filter paper or strip, which contains the labeled physiologically reactive species of this invention. Such elements can also contain a receptor for a specific binding assay immobilized in a suitable manner and kept isolated from the corresponding ligand analog prior to the assay. Such elements are known in the art as test strips, diagnostic elements, dip sticks, diagnostic agents and the like.

When employed in dry analytical elements, the ligand analog of this invention can be incorporated into a suitable carrier material by imbibition or impregnation, or can be coated on a suitable absorbent material. Useful carrier materials are insoluble and maintain their structural integrity when exposed to water or physiological fluids such as urine or serum. Useful carrier materials can be prepared from paper, porous particulate structures, cellulose, porous polymeric films, wood, glass fiber, woven and nonwoven fabrics (synthetic and nonsynthetic) and the like. Useful materials and procedures for making such elements are well known in the art as exemplified in U.S. Pat. No. 3,092,465 (issued June 4, 1963 to Adams et al), U.S. Pat. No. 3,802,842 (issued April 9, 1974 to Lange et al), U.S. Pat. No. 3,915,647 (issued Oct. 28, 1975 to Wright), U.S. Pat. No. 3,917,453 (issued Nov. 4, 1975 to Milligan et al), U.S. Pat. No. 3,936,357 (issued Feb. 3, 1976 to Milligan et al), U.S. Pat. No. 4,248,829 (issued Feb. 3, 1981 to Kitajima et al), U.S. Pat. No. 4,255,384 (issued Mar. 10, 1981 Kitajima et al), and U.S. Pat. No. 4,270,920 (issued June 2, 1981 to Kondo et al), and U.K. Pat. No. 2,052,057 (published Jan. 21, 1981).

Preferably, the dry analytical elements of this invention have at least one porous spreading zone as the absorbent carrier material. This zone can be self-supporting (i.e. composed of a material rigid enough to maintain its integrity), but preferably it is carried on a separate supporting substrate (commonly called a support). Such a support can be any suitable dimensionally stable, and preferably, transparent (i.e. radiation transmissive) material which transmits electromagnetic radiation of a wavelength between about 200 and about 900 nm. A support of choice for a particular element should be compatible with the intended mode of detection (reflection or transmission spectroscopy). Useful support materials include paper, metal foils, polystyrene, polyesters [e.g. poly(ethylene terephthalate)], polycarbonates, cellulose esters (e.g. cellulose acetate), etc.

The porous spreading zone can be prepared from any suitable fibrous or non-fibrous material or mixtures of either or both. The void volume and average pore size of this zone can be varied depending upon the use intended. For example, if whole blood or other liquid samples containing high molecular weight materials are to be assayed, the void volume and average pore size are generally greater than if serum or urine is to be assayed.

Useful spreading zones can be prepared using fibrous materials, either mixed with a suitable binder material or woven into a fabric, as described in U.S. Pat. No. 4,292,272 (issued Sept. 29, 1981 to Kitajima et al). Alternatively the spreading zone is prepared from polymeric compositions (e.g. blush polymers) or particulate materials, with or without binding adhesives, as described in U.S. Pat. Nos. 3,992,158 (issued Nov. 16, 1976 to Przybylowicz et al) and U.S. Pat. No. 4,258,001 (issued Mar. 24, 1981 to Pierce et al). Other useful spreading zone materials are described in W. German OLS No. 3,150,102 (published July 29, 1982) and Japanese Patent Publication 57(1982)-101760 (published June 24, 1982). It is desirable that the spreading zone be isotropically porous, meaning that the porosity is the same in each direction in the zone as created by interconnected spaces or pores between particles, fibers, polymeric strands, etc.

The elements can have one or more reagent zones, spreading zones, registration zones, mordant zones, radiation-blocking or filter zones, subbing zones, barrier zones, buffer zones, etc. The zones are generally in fluid contact with each other meaning that fluids, reagents and reaction products can pass between superposed regions of adjacent zones. Stated in another manner, fluid contact refers to the ability to transport components of a fluid between the zones in fluid contact. Preferably, the zones are separately coated layers, although two or more zones can be a single layer, or a zone can contain two or more separate layers.

The fluorescent labeled ligand analog of this invention can be incorporated in any zone of the element. Alternatively, it can be added to the test sample which is subsequently applied to the element, or the ligand analog can be separately (either subsequently or simultaneously) added to the element with the test sample. The receptor corresponding to the ligand to be determined can also be in any zone of the element in immobilized form, or added to the element simultaneously with the test sample. If both the ligand analog and the receptor are incorporated into the element prior to the assay, they must be kept isolated from each other until the assay is carried out.

In the elements of this invention, the coverage of the ligand analog can be varied widely, but it is generally present in a coverage of up to about 1, and preferably from about $10^{-6}$ to about 1 g/m². The receptor can be present in a coverage of up to about 200, and preferably from about 40 to about 200 g/m². A variety of other desirable, but optional, reagents and addenda can be present in the element in amounts known to one skilled in the art. Such materials include interactive reagents, surfactants, buffers, binders, pigments, activators, etc.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, determination of a ligand is made by taking the element from a supply roll, chip packet or other source and physically contacting it with a sample (e.g. 1-100 ul) of the liquid to be tested in the presence of the receptor. Such contact can be accomplished in any suitable manner, e.g. dipping or immersing the element into the sample or, preferably, by spotting the element by hand or machine with a drop of the sample with a suitable dispensing means.

After sample application, the element is exposed to any conditioning, such as incubation, heating or the like, that may be desirable to quicken or otherwise facilitate obtaining any test result. Determination of the ligand is achieved by measuring the fluorescence of either the bound (i.e. complexed) or unbound (i.e. non-complexed) labeled ligand analog.

The following examples are presented to illustrate the practice of the present invention. In these examples, the materials were obtained as follows: N-carbobenzoxyglycylglycine from Sigma Chemical Co. (St. Louis, Mo.), cyclohexylmorpholinoethylene glycol (mol. wt. 750) from Aldrich Chemical Co. (Milwaukee, Wis.), sodium cyanoborohydride from Alfa Products (Danvers, Mass.), pellitized carbon black from Cabots Chemical Co. (Boston, Mass.), poly(vinyl butyral) from Monsanto Co. (St. Louis, Mo.), bovine gamma globulin (BGG) from Miles Laboratories, Inc. (Naperville, Ill.), Zonyl FSN ™ surfactant from DuPont (Wilmington, Del.), *Staphylococcus aureus* particles from Calbiochem-Behring (LaJolla, Calif.), sodium periodate from Fisher Scientific Co. (Rochester, N.Y.), Dextran B1355 from Dr. M. D. Slocki (Biochemistry Research Fermentation Laboratories, Peoria, Ill.), Dextran T70, T10 and 500 and Sepharose ™ 2B/6B from Pharmacia Fine Chemicals (Piscataway, N.J.), inulin from Sigma Chemical Co. (St. Louis, Mo.), and the remaining 5 reagents were either prepared using conventional procedures or obtained from Eastman Organic Chemicals (Rochester, N.Y.).

EXAMPLE 1

Europium Labeled-Dextran Ligand Analog for Determining Thyroxine

A fluorescent labeled ligand analog of the present invention useful for the determination of the ligand thyroxine was prepared in the following manner:

Synthesis of Thyroxine Methyl Ester

Thyroxine (20 g) was suspended in dry methanol (500 ml). The suspension was saturated with hydrogen chloride gas, cooled and saturated again. The crystals were collected, washed with methanol and ether, and then dried. The resulting thyroxine methyl ester hydrochloride crystals were added to 500 ml of methanol and an equimolar concentration of concentrated sodium hydroxide was added with stirring. Deionized distilled water (500 ml) was added to this solution. The solution was chilled to recrystallize the thyroxine methyl ester from the solution. The crystals were then collected and air dried.

Synthesis of N-carbobenzoxyglycylglycylthyroxine Methyl Ester

Thyroxine methyl ester (5 g), as prepared above, N-carbobenzoxyglycylglycine (1.67 g) and cyclohexylmorpholinoethylcarbodiimide (5.3 g) were combined in 40 ml of dimethylacetamide. The mixture was stirred at room temperature for 24 hours, poured into deionized water, and the resulting residue collected and washed with water. The residue was recrystallized from methanol and water, yielding the product, N-carbobenzoxyglycylglycylthyroxine methyl ester.

Synthesis of Glycylglycylthyroxine Methyl Ester Hydrobromide

N-carbobenzoxyglycylglycylthyroxine methyl ester (2.3 g), as prepared above, was suspended in 60 ml of hydrobromic and acetic acids (31% HBr in acetic acid). The mixture was stirred at room temperature for 5 hours. The resulting hydrobromide salt was collected by precipitation with ether, filtered, washed with ether and dried in vacuo to yield glycylglycylthyroxine methyl ester hydrobromide.

Oxidation of Dextran Polysaccharides

Several dextran polysaccharides were oxidized in preparation for covalently bonding the thyroxine component thereto.

A. Dextran B1355 was oxidized by the following procedure: 2 g of the polysaccharide was dissolved in 200 ml deionized, distilled water. Solid sodium periodate (0.43 g) was added and the pH was adjusted to 6.0. The reaction was stirred at room temperature for 1 hour and then dialyzed extensively against distilled running water. The product shown below was obtained by lyophilization.

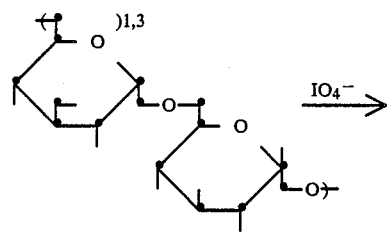

Dextran B1355

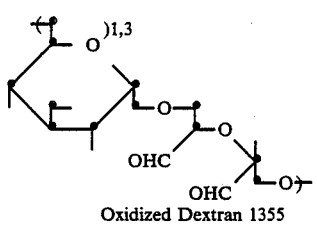

Oxidized Dextran 1355

B. Dextran T-70 (4 g) was oxidized as described in part A above with the following exceptions: 4 g of Dextran T-70 was dissolved in 80 ml of deionized distilled water and 0.86 g of sodium periodate was added.

C. Dextran T-10 (4 g) was oxidized as described in part B above.

Synthesis of Thyroxine Methyl Ester Dilycyl Dextran Conjugates

Thyroxine methyl ester diglycyl polysaccharide conjugates were prepared by reduction of the Schiff base formed between the amine of thyroxine methyl ester glycylglycine and the aldehydes of the oxidized dextrans with sodium cyanoborohydride. Reaction conditions were designed to obtain various thyroxine-to-polysaccharide ratios.

Oxidized Dextran B1355 (0.114 g) was dissolved in 10 ml of 0.2 molar potassium phosphate buffer, pH 8.0. Diglycylthyroxine methyl ester hydrobromide (0.034 g) was dissolved in 2 ml of dimethylacetamide and was then added to the polysaccharide solution, followed by the addition of 0.06 g of sodium cyanoborohydride. The reaction was stirred at room temperature for 2-3 days. The solution was then dialyzed extensively against 25% dimethyl formamide in water, followed by dialysis against distilled water and lyophilization to obtain the product.

The concentration of thyroxine in the resulting thyroxine-polysaccharide conjugate was determined spectrophotometrically at 325 nm against a known concentration of thyroxine-polysaccharide conjugate with an extinction coefficient of 6300. From this data, the unknown thyroxine-to-polysaccharide ratio was calculated.

Conjugates using the oxidized Dextrans T-70 and T-10 were similarly prepared.

Formation of Ligand Analogs

The diglycyl thyroxine methyl esterpolysaccharide conjugates described above were adsorbed onto the surface of various labeled polymer latex particles in loaded latices to form ligand analogs. Various hapten-polysaccharide conjugate to latex ratios were used in these preparations. The preparation of diglycyl thyroxine methyl ester-polysaccharide-europium ($Eu^{+3}$) chelate-loaded poly(styrene-co-acrylamide-co-methacrylic acid) (weight ratio 85/10/5) summarized below is representative. Diglycyl thyroxine methyl ester-Dextran B1355 (22 mg) (thyroxine:Dextran ratio of 10,881:1) was suspended in 3 ml of deionized distilled water. An amount of the latex equivalent to 1 ml of 8% solids, was added dropwise with stirring to the suspension. The reaction was stirred at room temperature for 2-5 days and was then chromatographed on a Sepharose ™ 2B/68 column. The latex band was collected and assayed for percent solids and iodine content. The hapten-polysaccharide conjugate to latex ratio, which ranged from 1.4:1 to 4.4:1, was determined from these results.

The method described above was used to prepare the following labeled ligand analogs using the indicated latices and thyroxine-polysaccharide conjugates.

Poly(styrene-co-acrylamide-co-methacrylic ($Eu^{+3}$ chelate) (weight ratio 85/10/5) was sensitized with the following conjugates:

diglycyl thyroxine methyl ester-Dextran B1355 (6889:1 thyroxine:polysaccharide ratio)

diglycyl thyroxine methyl ester-Dextran T-70 diglycyl thyroxine methyl ester-Dextran T-10 In addition, the following latex copolymers were sensitized with diglycyl thyroxine methyl esterDextran B1355 (10,881:1 thyroxine:polysaccharide ratio).

poly(styrene-co-methacrylamide-co-methacrylic acid) (weight ratio 85/10/5) ($Eu^{+3}$ chelate)

poly(styrene-co-methacrylic acid) (weight ratio 95/5) ($Eu^{+3}$ chelate)

polystyrene ($Eu^{+3}$ chelate)

poly(styrene-co-acrylamide) (weight ratio 90/10) chelate)

poly(hydroxymethylstyrene-co-acrylamide-comethacrylic acid) (weight ratio 85/10/5) ($Eu^{+3}$ chelate)

poly[styrene-co-acrylamide-co-2-(2-methacryloyloxyethylamino)-4,6-dichloro-5-triazine](weight ratio 88/10/2) ($Eu^{+3}$ chelate)

EXAMPLE 2 - Evaluation of labeled Thyroxine Analog

An evaluation of a thyroxine analog was carried out in solution in the following manner using the labeled ligand analog diglycyl thyroxine methyl ester-Dextran B1355-poly(styrene-co-acrylamide-co-methacrylic acid) (weight ratio 85/10/5) ($Eu^{+3}$ chelate) prepared as described in Example 1 hereinabove.

This lgand analog was evaluated as a label for a thyroxine assay by considering the following factors:

(1) The ability of the ligand analog to specifically bind to antithyroxine receptor.

(2) The ability of the specific binding with the receptor to be reversed in the presence of free thyroxine.

(3) Nonspecific binding of the ligand analog to antibodies not receptors for thyroxine.

The labeled thyroxine analog noted above was diluted to 0.01125% solids in glycine acetate buffer (pH 7) and combined with serially diluted high titer thyroxine antiserum in glass microculture tubes. Antiserum dilutions ranged from 1:6 to 1:192. After overnight incubation at room temperature, the tubes were evaluated under ultraviolet light for agglutination. Agglutination was observed with antiserum dilutions up to and including the 1:192 dilution. This demonstrated the first factor noted above.

The reversal of the analog-antibody binding in the presence of free thyroxine was examined by adding free thyroxine ($3.3 \times 10^{-6}$ molar final concentration) to the assay described above. No agglutination of the labeled latex was observed indicating that free thyroxine caused the analogantibody binding to be reversed. This demonstrates the second factor noted above.

The thyroxine analog was also incubated with serial dilutions of antibovine gamma globulin (anti-BGG) which is not a receptor for thyroxine. No agglutination was observed demonstrating the third factor noted above.

EXAMPLE 3

Europium Labeled-Lipopolysaccharide Thyroxine Analog

A thyroxine analog useful for the determination of thyroxine was prepared in the following manner:

Synthesis of Thyroxine Polyethyleneglycol Ester Hydrochloride

L-Thyroxine (5 g) was suspended in 40 g of molten monomethoxypolyethyleneglycol (mol. wt. 750) and gently heated on a hot plate while saturating with HCl. Stirring was continued for an additional hour and the solution again saturated with HCl. After 2 hours, water (200 ml) was added and the precipitate collected and thoroughly washed with cold water and freeze dried to give the product which was used in the following preparatory steps.

Preparation of Fatty Acid-Polysaccharide (Lipopolysaccharide)

Polysaccharides were acrylated by reaction with fatty acid chlorides in pyridine as described by Tsumita et al in J. Exp. Med., 119, pp. 1017-1025 (1964). The preparation of palmitoyl-polysaccharide which follows is representative.

Dextran 70 (10 g) was suspended in 100 ml of pyridine. Ten ml of palmitoyl chloride was added dropwise with stirring. After stirring for 72 hours at room temperature, the mixture was poured into isopropanol, washed with isopropanol and ether, and dried. The product yield was 11.5 g.

A similar procedure was used to prepare the following:
Palmitoyl-Inulin
Palmitoyl-Dextran 500
Palmitoyl-Dextran B1355

Oxidation of the various Dextran and inulin lipopolysaccharides was accomplished according to the procedure described for the oxidation of the polysaccharides in Example 1 hereinabove.

Synthesis of Palmitoyl-Polysaccharide-Thyroxine Ester

Esterified thyroxine was covalently bound to the oxidized lipopolysaccharides by the formation and subsequent reduction in the presence of sodium cyanoborohydride of a Schiff base. The following method of preparation of palmitoyl-Dextran 70-diglycylthyroxine methyl ester is representative.

Oxidized palmitoyl-Dextran 70 (0.5 g), as prepared above, was dissolved in 50 ml of 0.2 molar potassium phosphate buffer (pH 8.0). Diglycylthyroxine methyl ester hydrobromide, from above(150 mg), in 10 ml dimethylacetamide was added, followed by the addition of 100 mg sodium cyanoborohydride. The mixture was stirred for 18 hours at room temperature, dialyzed against 25% N,N-dimethylformamide in water and lyophilized to yield the product.

Palmitoyl-inulin-diglycylthyroxine methyl ester and palmitoyl-Dextran B1355-diglycylthyroxine methyl ester were similarly prepared. Both conjugates were prepared from the hydrobromide salts of thyroxine esters.

A similar procedure was used for the production of conjugates made from hydrochloride salts of thyroxine esters, such as diglycylthyroxine methyl ester hydrochloride and thyroxine-polyethylene glycol ester hydrochloride, with the following exceptions: the oxidized lipopolysaccharides were dissolved in 0.1 molar potassium phosphate buffer (pH 7.0), the ester was dissolved in N,N-dimethylformamide, and following stirring the product was collected by precipitation from methanol, thoroughly washed with N,N-dimethylformamide, redissolved and dialyzed with water and lyophilized. Using this procedure, the following conjugates were prepared: palmitoyl-Dextran 70-thyroxine polyethylene glycol ester and palmitoyl-Dextran 500-thyroxine diglycyl and polyethylene glycol esters.

Thyroxine ester-oleyl polysaccharide conjugates were also prepared.

Oleyl-Polysaccharide Preparation

Carboxymethylated Dextran 70-thyroxine methyl ester (thyroxine:Dextran ratio of 9:1) and carboxymethyl cellulose were acylated with oleic acid chloride using a similar procedure as above with the exception that following incubation with stirring the product was washed with isopropanol and acetone before drying. In addition, the oleyl-carboxymethyl cellulose preparation was stirred for only 4 hours with gentle heating.

Oleyl-Carboxymethyl Cellulose-Diglycylthyroxine Methyl Ester Preparation

Oleyl-carboxymethyl cellulose (0.5 g) was dissolved in 10 ml of distilled water. Cyclohexylmorpholinoethylcarbodiimide metho-p-toluenesulfonate (0.5 g) and diglycylthyroxine methyl ester hydrobromide (0.3 g), in 10 ml dimethylacetamide, were added. The mixture was stirred for 18 hours at room temperature. The product was precipitated by the addition of methanol, washed thoroughly in succession with methanol, N,N-dimethylformamide, and methanol, dialyzed against distilled water, and lyophilized.

General Procedure for Preparation of a Ligand Analog

A fatty acid-polysaccharide-thyroxine conjugate (50 mg) was added to 5 ml of potassium phosphate buffer (0.01–0.05 molar, pH 6-8). A suitable labeled latex (5–8% solids) was then added dropwise with stirring to the conjugate solution. The final weight ratio of conjugate to latex solids was in the range of 1:5 to 1:2. The resulting suspensions were allowed to stir at room temperature for 24 hours and then purified by chromatography on Bio Gel A-5 or Sepharose 2B/6B supports.

Table I hereinbelow lists the conjugate and labeled latex components of the thyroxine analogs so prepared.

TABLE I

| Conjugate | Polymer Latex |
|---|---|
| Palmitoyl-Dextran 70-diglycyl thyroxine methyl ester | Poly(m,p-vinyltoluene) ($Eu^{+3}$ chelate) |
| Palmitoyl-Dextran 70-diglycyl thyroxine methyl ester | Polystyrene ($Eu^{+3}$ chelate) |
| Palmitoyl-Dextran 70-diglycyl thyroxine methyl ester | Poly(styrene-co-acryl amide-co-methacrylic acid) (weight ratio 85/10/5) ($Eu^{+3}$ chelate) |

TABLE I-continued

| Conjugate | Polymer Latex |
|---|---|
| *Palmitoyl-Dextran 70-thyroxine polyethylene glycol ester | |
| *Palmitoyl-Dextran 500-diglycyl thyroxine methyl ester | |
| *Palmitoyl-Dextran 500-thyroxine polyethylene glycol ester | |
| *Palmitoyl-Dextran B1355-diglycyl thyroxine methyl ester | |
| Palmitoyl-Dextran 500-thyroxine polyethylene glycol ester | Poly(m,p-vinyltoluene) (Eu$^{+3}$ chelate) |
| Oleyl-carboxymethylated Dextran 70-thyroxine methyl ester | |
| Oleyl-carboxymethyl cellulose-diglycyl thyroxine methyl ester | |
| Oleyl-hydroxypropyl-carboxymethyl cellulose-diglycyl thyroxine methyl ester | Polystyrene (Eu$^{+3}$ chelate) |
| Palmitoyl-inulin-diglycyl thyroxine methyl ester | Polystyrene (Eu$^{+3}$ chelate) |
| Palmitoyl-inulin-diglycyl thyroxine methyl ester | Poly(m,p-vinyltoluene) (Eu$^{+3}$ chelate |
| Palmitoyl-inulin-diglycyl thyroxine methyl ester | Poly(styrene-co-acrylamide-co-methacrylic acid) (weight ratio 85/10/5) (Eu$^{+3}$ chelate) |

*Each of these conjugates was individually adsorbed on labeled latex particles of both poly(m,p-vinyltoluene) (Eu$^{+3}$ chelate) and poly(styrene-co-acrylamide-co-methacrylic acid) (weight ratio 85/10/5) (Eu$^{+3}$ chelate).

EXAMPLE 4

Evaluation of Labeled Thyroxine Analog

An evaluation of a labeled thyroxine analog was carried out in solution in the following manner using the ligand analog palmitoyl-Dextran B1355-diglycyl thyroxine methyl ester poly(styrene-co-acrylamide-co-methacrylic acid) (weight ratio 85/10/5) (Eu$^{+3}$ chelate) prepared as described in Example 3 hereinabove.

This evaluation was carried out in a fashion comparable to the evaluation described in Example 2. Specific binding of the thyroxine analog to the antithyroxine receptor was obtained up to and including a 1:96 dilution of the antiserum. This binding was completely reversed in the presence of free thyroxine. No specific binding of the analog to anti-bovine gamma globulin was observed indicating the usefulness of this analog for thyroxine immunoassay

EXAMPLE 5

Solution Immunoassay for Phentoin (Dilantin)

Synthesis of 5,5-Dihenlhydantoin-3-(4-Butlamine Acetate)

5,5-Diphenylhydantoin, sodium salt (10 g) and 4-bromobutylnitrile (5.4 g) were combined in 75 ml N,N-dimethylformamide. The reaction mixture was stirred under nitrogen at 80°-90° C. for 1 hour. The N,N-dimethylformamide was removed under vacuum, and the product (5,5-diphenylhydantoin-3-butylnitrile) was recrystallized from methanol/acetonitrile and was hydrogenated using PtO as the catalyst in glacial acetic acid under nitrogen. After the hydrogenation, the catalyst was removed by filtration through a course sintered glass funnel containing celite. The solvent was then removed by evaporation and the resulting crude product was recrystallized from methanol/ethyl acetate.

Synthesis of a Phentoin-butylamine Polysaccharide Conjugate

A conjugate was synthesized from 5,5-diphenylhydantoin-3-(4-butylamine acetate) and Dextran T-70 by the procedure described in Example 1 for the synthesis of the thyroxine-Dextran conjugates.

Preparation and Use of Labeled Phenytoin Analog

The conjugates described above were absorbed onto the surface of Eu$^{+3}$-labeled poly(styrene-co-acrylamide-co-methacrylic acid) (weight ratio 85/10/5) latex particles by the procedure described in Example 1.

The resulting phenytoin analog was evaluated in an immunoassay in the following manner. Antiphenytoin antibody immobilized on *Staphylococcus aureus* particles (5 mg) in 50 1 buffer (0.01 molar potassium phosphate, 0.15 molar NaCl, pH 7.2) and increasing levels of phenytoin ($2 \times 10^{-9}$ molar to 2 x 10- molar, 100 1) were dispensed into small tubes. Phenytoin analog (1:1000 dilution) (50 μl) was added to each tube. The tube contents were then mixed, incubated at room temperature for 30 minutes and centrifuged. The supernatent (100 μl) was removed from each tube and combined with 900 μl of water in a polystyrene microabsorbance cell and the resulting fluorescence was measured. As shown in the following table, the fluorescence generally increased with increasing phenytoin levels greater than 1 nanomolar.

| Phenytoin (nanomolar) | Fluorescence (nano A) |
|---|---|
| 0 | 0.30 |
| 1 | 0.29 |
| 10 | 0.38 |
| 100 | 0.57 |
| 1000 | 0.92 |
| 10,000 | 1.0 |
| 100,000 | 1.0 |

EXAMPLE 6

Dry Analytical Element and its Use in Immunoassay for Bovine Gamma Globulin

A dry element was used to assay for bovine gamma globulin (BGG) in the following manner.

A lipopolysaccharide obtained by oxidizing palmitoyl Dextran B1355 in 10$^{-2}$ molar periodate, followed by dialysis and recovery by lyophilization, was absorbed directly onto the surface of Eu$^{+3}$ chelate-containing latex particles of poly(styrene-co-acrylamide-co-methacrylic acid) (weight ratio 85/10/5) to form a fluorescent label. For the performance of a fluorescent immunoassay agglutination test, BGG antigen was incubated with the fluorescent label in the presence of a selective reducing agent, sodium cyanoborohydride. The resulting ligand analog was purified by gel chromatography on agarose to remove an noncovalently bound BGG.

The activity of the labeled analog was demonstrated using a dry test element having the following format and components:

| | Range g/m$^2$ |
|---|---|
| Polystyrene beads having anti-BGG antibody adsorbed thereto | 40–200 |
| Poly(n-butylacrylate-co-styrene-co-2-acrylamido-2-methylpropane sulfonic acid) (weight ratio 70/20/10) adhesive | 1–15 |
| Zonyl FSN ™ surfactant | 0.1–5 |
| Potassium chloride | 0.1–2 |
| Boric acid | 0.1–2 |
| Pellitized carbon black | 0.1–10 |
| Poly(vinyl butyral) | 0.1–10 |
| Poly(ethylene terephthalate) Support | |

Mixtures of labeled BGG at $10^{-8}$ molar and unlabeled BGG at $10^{-9}-10^{-5}$ molar were prepared. A 10 μl sample of each mixture was spotted onto a sample of the element. All element samples were incubated for 1–3 minutes at 37° C., after which a phosphate buffer (pH 7.5) saline wash solution was applied to remove unbound BGG. A dose response curve generated by measuring the bound fluorescent label in the element indicated that as unlabeled BGG concentration increased, the amount of bound labeled BGG decreased.

EXAMPLE 7

Dry Analytical Element and Its Use in Immunoassay for Thyroxine

An element was prepared similar to that described in Example 6 except that anti-thyroxine antibody was immobilized on the polystyrene beads in place of anti-BGG. A fluorescent labeled thyroxin analog ($10^{-10}$ molar) as described in Example 1 and unlabeled thyroxine samples ($10^{-9}-10^{-6}$ molar) were applied to samples of the element by the procedure described in Example 6. After a one minute incubation, the element samples were washed with a phosphate buffer (pH 7) saline solution to remove unbound thyroxine. The presence of bound labeled thyroxine remaining in the element was evaluated by measure of the fluorescence. A dose response curve generated from the data indicated that the higher the unbound thyroxine concentration in the test sample, the lower the amount of bound labeled thyroxine in the element.

EXAMPLE 8

Stability Comparison

This example illustrates the improved stability of the immunoreagent compositions of this invention by comparing them to similar compositions taught in the art, namely those taught in U.S. Pat. No. 4,283,382 (noted hereinabove). This comparison was carried out in the following manner.

Fluorescent labels ($Eu^{+3}$ chelate) were prepared according to the teaching of U.S. Pat. No. 4,283,382 using poly(styrene-co-methacrylic acid) (weight ratio 95/5) (latex 1) and poly(styrene-co-acrylamide) (weight ratio 90/10) (latex 2). Thyroxine methyl ester glycyl glycyl Dextran B conjugate was absorbed to the polymeric particles of a portion of each $Eu^{+3}$-containing latex noted above at a ratio of 1.2:1 (latex 1) and 0.8:1 (latex 2), respectively, to form thyroxine analogs. All four preparations were stored at 10° C. for several months after which they were evaluated for stability.

Large clumps of precipitated latex were observed in both preparations of fluorescent labels prepared according to the prior art while substantially no precipitated latex was observed in the preparations containing thyroxine analog.

The invention has been described in detail with particular reference to preferred embodiments thereof, but it will be understood that variations and modifications can be effected within the spirit and scope of the invention.

We claim:

1. A fluorescent label comprising a polysaccharide bound to a polymeric particle which is derived from a loadable latex having a discontinuous phase which consists essentially of a polymer prepared from one or more ethylenically unsaturated polymerizable monomers, and an aqueous phase, said polymeric partilce having incorporated therein a fluorescent rare earth chelate.

2. The label of claim 1 wherein said polysaccharide is a dextran or lipopolysaccharide and has a molecular weight of from about $10^4$ to about $10^7$ daltons.

3. The label of claim 1 wherein the chelate is a chelate of europium or terbium and a 1,3-diketone, phthalate, naphthoate, dipyridine, terpyridine or phenanthroline chelating agent.

4. The label of claim 1 wherein said polymer comprises (a) from 0 to 100 weight percent of units derived from a styrene or vinyl naphthyl monomer, (b) from 0 to about 90 weight percent of units derived from an ethylenically unsaturated monomer of the structure 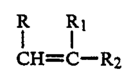 wherein R is hydrogen or alkyl, $R_1$ is hydrogen or methyl, $R_2$ is hydrogen, halogen, alkyl, cyano, or wherein $R_3$ is hydrogen or $R_4$, and $R_4$ is an aliphatic group, and (c) from 0 to about 10 weight percent of units derived from an ethylenically unsaturated monomer containing one or more sulfonic acid or carboxy groups, or an ammonium or alkali metal salt thereof.

* * * * *